(12) United States Patent
Fleischman et al.

(10) Patent No.: US 6,623,984 B1
(45) Date of Patent: Sep. 23, 2003

(54) MEMS-BASED INTEGRATED MAGNETIC PARTICLE IDENTIFICATION SYSTEM

(75) Inventors: Aaron J. Fleischman, University Heights, OH (US); Shuvo Roy, Cleveland, OH (US); Jeff Chalmers, Columbus, OH (US); Maciej Zborowski, Bay Village, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 202 days.

(21) Appl. No.: 09/704,298

(22) Filed: Nov. 1, 2000

(51) Int. Cl.⁷ .............................................. G01N 33/553
(52) U.S. Cl. ...................... 436/526; 436/501; 436/518; 436/514; 422/50; 422/51; 422/68.1; 422/82.05; 422/82.08; 422/186; 422/186.1; 435/287.2; 435/287.3; 435/287.1; 210/695; 210/95; 210/222; 210/450; 209/214; 209/223.1
(58) Field of Search ................... 422/50, 51, 68.1, 422/82.05, 82.08, 186, 186.1; 436/526, 501, 518, 514; 435/287.2, 287.03, 287.1; 210/695, 95, 222, 450; 209/214, 223.1

(56) References Cited

U.S. PATENT DOCUMENTS

| | | | |
|---|---|---|---|
| 3,924,947 A | | 12/1975 | Hogg |
| 4,548,500 A | | 10/1985 | Wyatt et al. |
| 5,515,163 A | | 5/1996 | Kupershmidt et al. |
| 5,655,665 A | | 8/1997 | Allen et al. |
| 5,714,059 A | * | 2/1998 | Seifert et al. |
| 5,726,751 A | | 3/1998 | Altendorf et al. |
| 5,918,272 A | | 6/1999 | Snyder et al. |
| 5,927,325 A | * | 7/1999 | Bensaoula et al. |
| 5,932,100 A | | 8/1999 | Yager et al. |
| 5,941,481 A | * | 8/1999 | Snarski |
| 5,968,820 A | * | 10/1999 | Zborowski et al. |
| 5,971,158 A | | 10/1999 | Yager et al. |
| 5,974,901 A | * | 11/1999 | Zborowski et al. |
| 5,992,820 A | * | 11/1999 | Fare et al. |
| 5,993,630 A | | 11/1999 | Becker et al. |
| 5,993,632 A | | 11/1999 | Becker et al. |
| 6,082,205 A | * | 7/2000 | Zborowski et al. |
| 6,105,424 A | | 8/2000 | Fay et al. |
| 6,120,735 A | * | 9/2000 | Zborowski et al. |
| 6,133,046 A | | 10/2000 | Clerc |
| 6,156,208 A | * | 12/2000 | Desjardins et al. |
| 6,355,491 B1 | * | 3/2002 | Zhou et al. |
| 6,412,359 B1 | * | 7/2002 | Zborowski et al. |
| 6,432,630 B1 | * | 8/2002 | Blankenstein |
| 6,454,924 B2 | * | 9/2002 | Jedrzejewski et al. |
| 6,485,690 B1 | * | 11/2002 | Pfost et al. |
| 6,495,892 B2 | * | 12/2002 | Goodman et al. |

\* cited by examiner

*Primary Examiner*—Christopher L. Chin
*Assistant Examiner*—Pensee T. Do
(74) *Attorney, Agent, or Firm*—Tarolli, Sundheim, Covell & Tummino L.L.P.

(57) ABSTRACT

The present invention provides a MEMS-based integrated particle identification system having a substrate, a magnetic structure, and a bioferrograph. The substrate includes a topside portion, backside portion and a flow system. The flow system includes a flow channel for accepting the flow of a stream of particles to identified. The magnetic structure is in physical communication with the topside and backside portions of the substrate and has at least two pole pieces. A plurality of pole piece embodiments are provided for generating a magnetic field that acts on magnetically susceptible particles in the flow stream. The bioferrograph has at least one sensor for identifying the presence and quantity of magnetically susceptible particles. A plurality of sensor embodiments are also provided.

21 Claims, 9 Drawing Sheets

MEMS-BASED INTEGRATED MAGNETIC PARTICLE IDENTIFICATION SYSTEM

FIELD OF THE INVENTION

The invention relates generally to particle identification systems, and more particularly, to micro electromechanical systems (MEMS) and methods for identifying and quantifying magnetically susceptible particles through magnetic sorting and bioferrography.

BACKGROUND OF THE INVENTION

Cell and pathogen analysis is an increasingly important technique in the diagnosis and treatment of various cancers and diseases. Of primary importance to this analysis is the ability to separate, identify and quantify cells and pathogens. In such an analysis, the identification of differentiating cell properties allows such properties to be used as "handles" which, in turn, can be used to separate cells or particles from other cells or particles. Among the most commonly used "handles" for sorting cells and other microbes are immunological labels that include, for example, immunofluorescent and immunomagnetic labels. Immunofluorescent labels typically include, for example, a fluorescent molecule joined to an antibody. Immunomagnetic labels typically include, for example, a paramagnetic compound or molecule joined to either a primary or secondary antibody. Cell labeling is performed by attaching the antibody to a marker of interest on the surface of the cell (i.e., cell surface marker).

In the case of immunomagnetically label cells, a magnetic field can be used to separate such cells based on their magnetic susceptibility. For example, U.S. Pat. No. 5,968,820 to Zborowski et al., which is hereby fully incorporated by reference, describes methods and apparatuses for magnetically separating cells into fractionated flow streams. More specifically, through a combination of flow compartments and one or more magnetic fields, a flow stream of heterogeneous cells is separated into fractionated flow streams based on cell magnetic susceptibility. The fractionated flow streams are then collected and the particles recovered therefrom.

By superposition, a sample of unknown cells can be identified by using the above apparatus and an antibody cocktail. The unknown cell population can be mixed with various antibodies (antibody cocktail) to screen for the presence of suspected cell populations. If in a sample one suspects pathogens A, B, C or D to be present, one mixes magnetically tagged antibodies of anti-A, anti-B, anti-C and anti-D. When the fluid stream of tagged cells is placed in a magnetic field, the force imparted on the magnetically tagged cells causes the cells to jump flow lines and move laterally into the carrier fluid. The total force imparted on the cell, which is a function of cell geometry and the cells dipole moment, determines the lateral distance that the tagged cell moves into the carrier fluid. Thus, different types of cells all immunomagnetically tagged will move different distances. If laminar flow and precise geometry can be maintained, cell types can be identified by their lateral distribution MEMS technology creates high-precision microscopic structures on silicon. Through MEMS technology, relatively low-cost, high-volume, electromechanical systems that integrate sensors, actuators, electronics, and other components can be realized on a miniature scale. Hence, it would highly desirable to provide a MEMS-based system for identifying and quantifying magnetically susceptible particles.

SUMMARY OF THE INVENTION

According to one embodiment of the present invention, a MEMS-based integrated particle identification system employing an antibody cocktail is provided. Particles suitable for separation by the present invention include organic and non-organic particles. Organic particles preferably include, for example, cells, viruses, organelles, and DNA. Non-organic particles preferably include magnetic and paramagnetic particles such as, for example, metallic and non-metallic particles and molecules.

The system includes a substrate, a magnetic structure, and a bioferrograph is provided. The substrate includes a topside portion, backside portion and a flow system. The flow system includes a flow channel for accepting the flow of a stream of particles to identified. The magnetic structure is in physical communication with the topside and backside portions of the substrate and has at least two pole pieces. The pole pieces may be conventional flat pole pieces, may have contoured ends (e.g., hyperbolic) or each pole piece can have a plurality of discrete pole pieces generating a magnetic field that acts on magnetically susceptible particles in the flow stream. The bioferrograph has at least one sensor for identifying the presence and quantity of magnetically susceptible particles.

It is therefore an advantage of the present invention to provide a MEMS-based integrated particle identification system.

It is a further advantage of this invention to provide an integrated MEMS-based particle identification system that includes a bioferrograph.

It is a further advantage of the present invention to provide a MEMS-based magnetic structure for an integrated particle identification system.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to example the principles of this invention.

DETAILED DESCRIPTION OF ILLUSTRATED EMBODIMENT

Figure 1:
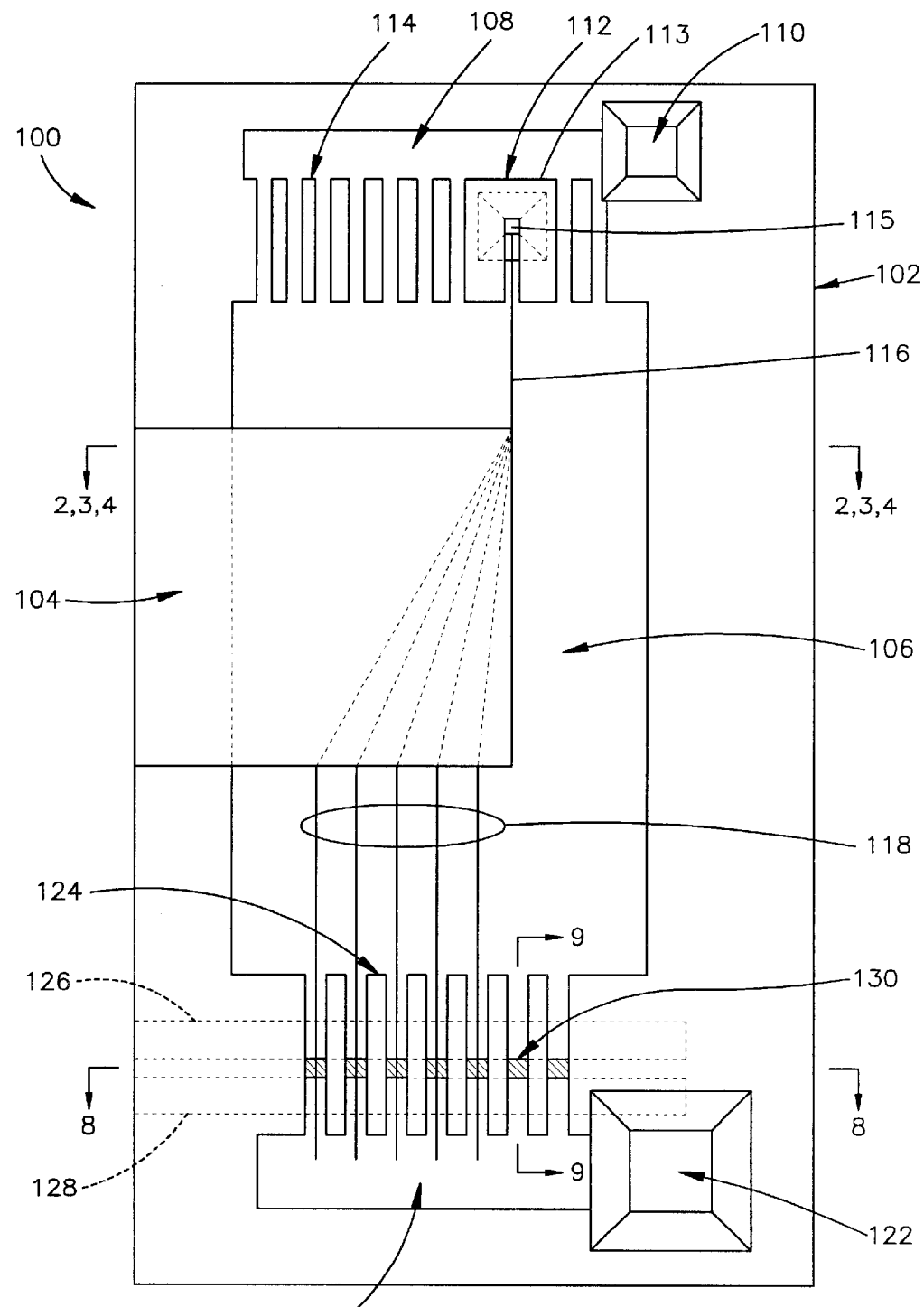
FIG. 1 is a plan view of one embodiment of a microfluidic chip of the present invention.

Referring now to the drawings, and more particularly to FIG. 1, a microfluidic chip 100 is shown. The chip 100 identifies a sample of unknown cells through the use of an antibody cocktail, and,cell migration. The unknown cell population is preferably mixed with various antibodies (antibody cocktail) to screen for the presence of suspected cell populations. Suitable antibodies preferably include, for example, immunological labels such as immunofluorescent and immunomagnetic markers. An immunofluorescent marker is a fluorescent molecule joined to an antibody. While an immunomagnetic label consists of a paramagnetic compound or molecule joined to either a primary or secondary antibody. The magnetic and fluorescent markers can be combined and joined to a single antibody creating an immunological label with both types of properties.

The chip 100 has a substrate portion 102 and a magnetic structure 104. The substrate portion 102 has a plurality of components including a flow channel 106, inlet manifold 108, and outlet manifold 120. The substrate portion 102 further has a carrier fluid inlet 110 which is in fluid communication with the inlet manifold 108. The carrier fluid inlet 110 provides the inlet manifold with carrier fluids that are fed into the flow channel 106 through a plurality of inlet flow dividers such as, for example, inlet flow divider 114.

A sample inlet structure 112 is located down stream of the carrier fluid inlet 110 and inlet manifold 108. More specifically, the sample inlet structure 112 has a divider component 113 that is incorporated as an inlet flow divider similar in nature to inlet flow divider 114. The divider component 113 further has within it a sample inlet 115 for feeding a sample of, for example, a heterogeneous cell population that includes, cells labeled with the antibody cocktail, into flow channel 106.

In fluid communication with the outlet manifold 120 is an outlet 122 and a plurality of outlet manifold dividers such as, for example, outlet flow divider 124. Outlet manifold dividers such as divider 124 divide the flow channel flow into two or more portions (eight are shown in FIG. 1) for detection by sensors such as, for example, sensor 130. As shown, each portion created by the outlet manifold dividers preferably includes at least one sensor. The sensors preferably work in combination with a second magnetic portion having a north magnetic pole piece 126 and a south magnetic pole piece 128. The sensors will be discussed in more detail in connection with FIGS. 10 through 15.

In operation, carrier fluid enters the inlet manifold 108 through carrier fluid inlet 110. Inlet flow dividers such as divider 114 split or divide the carrier fluid flow as it exits the inlet manifold 108 and enters the flow channel 106. Similarly, outlet manifold dividers such as divider 124 split or divide the flow as it exits the flow channel 106 and enters the outlet manifold 120. However, within the flow channel 106, the carrier fluid forms a plurality of laminar flow compartments in accord with the spacing of the inlet and outlet flow dividers such as dividers 114 and 124, respectively, and the carrier fluid flow rate. For more information on the formation of flow compartments, see U.S. Pat. No. 5,968,820 to Zborowski et al., which is hereby fully incorporated by reference.

A sample having a heterogeneous population of magnetically susceptible particles or cells is input into the flow channel 106 through sample inlet structure 112 and sample inlet 115. Upon initial entry into the flow channel 106, the sample is in the formed of a single flow stream 116. Magnetic structure 104 provides a substantially uniform force field within at least a portion of the flow channel and acts on the magnetically susceptible particles in flow stream 116. The effect of the substantially uniform force field on the magnetically susceptible particles is to cause the particles to migrate to varying degrees across the established flow compartments within the flow channel 106. The net effect of this migration is the formation of a plurality of sample flow streams 118 that include particles of identical or similar magnetic susceptibility. For more information on the use of flow compartments and substantially uniform magnetic fields to separate magnetically susceptible particles, see U.S. Pat. No. 5,968,820 to Zborowski et al., which is hereby fully incorporated by reference. After the original flow stream 116 has been fractionated or sorted into one or more sample flow streams 118, the one or more flow streams 118 are directed to a bioferrograph portion of chip 100. Generally, a bioferrograph magnetically manipulates cells within a fluid stream and deposits them onto a substrate. The bioferrograph portion of chip 100 includes sensors, such as sensor 130, that are located between the outlet flow dividers and magnetic pole pieces 126 and 128.

Figure 2:
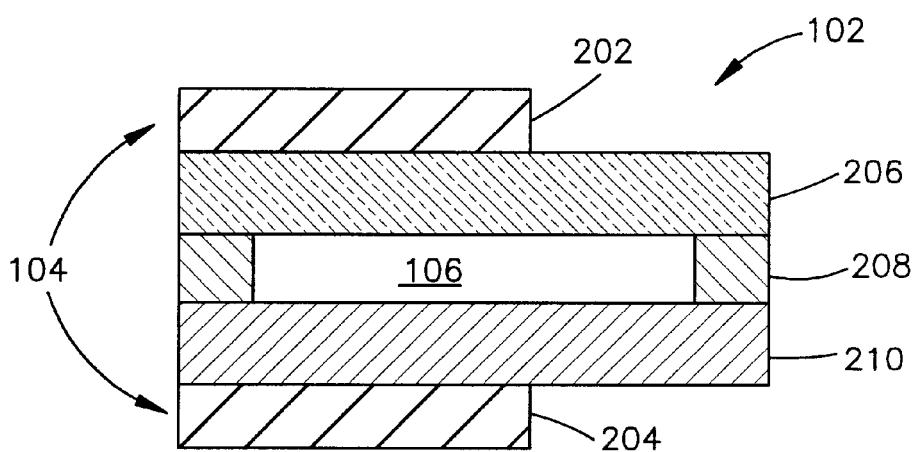
FIGS. 2, 3, and 4 are cross-sectional views taken along section lines 2—2, 3—3, and 4—4 of FIG. 1 illustrating various embodiments of a magnetic structure.
Figure 3:
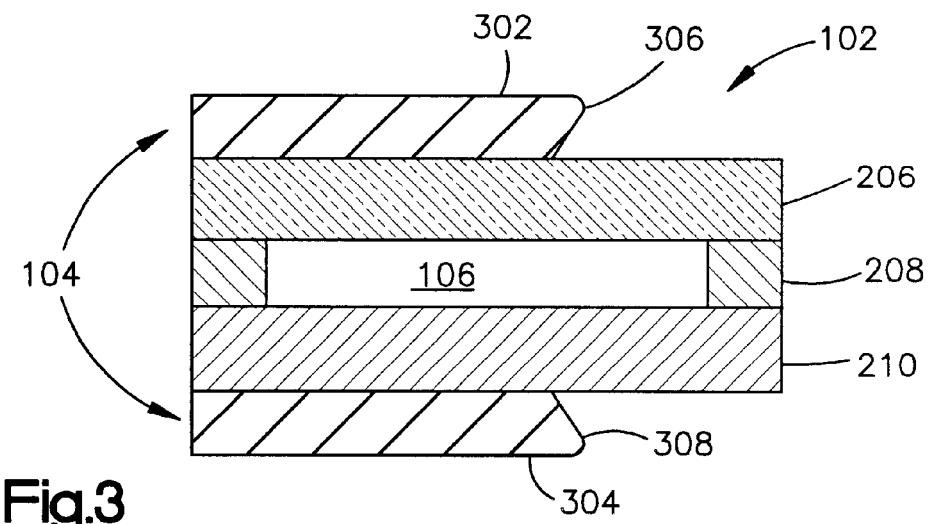
Figure 4:
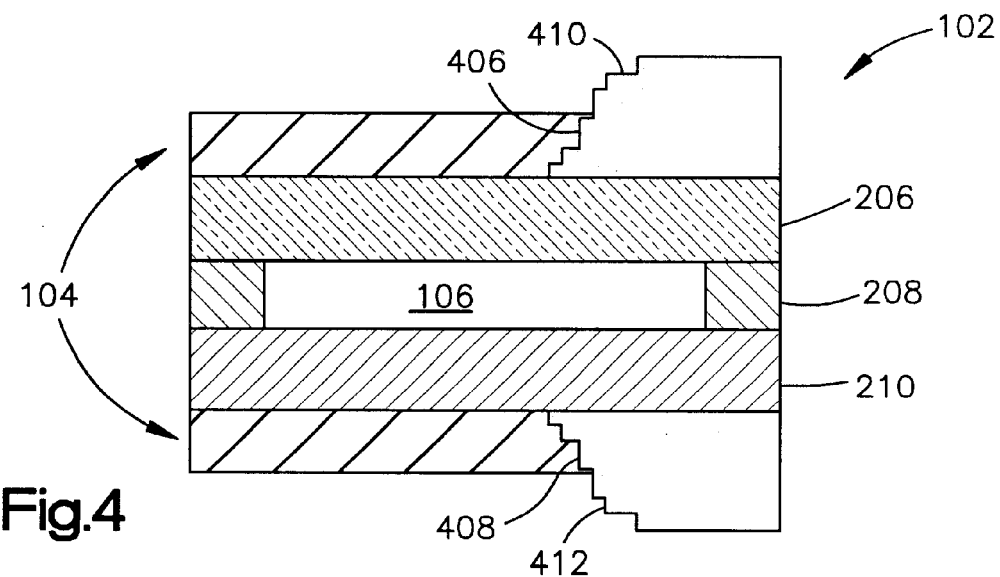

Referring now to FIGS. 2, 3, and 4, various embodiments of cross-sectional geometry are shown for the section taken through common section lines 2—2, 3—3, and 4—4 in FIG. 1. The, differences in the embodiments primarily relates to the magnetic structure 104. In this regard, the substrate portion 102 includes a plurality of material layers. In the described embodiment, substrate portion 102 is of a three layer construction having a glass layer 206 and silicon layers 208 and 210. Each layer's structure is formed on an individual wafer through Deep Reactive Ion Etching (DRIE) or micromachining. Hence, in FIGS. 2, 3, and 4, silicon layer 208 defines the shape and depth of the flow channel and inlet and outlet manifold architectures. Silicon layer 210 forms the substrate upon which the cell sensors are formed and hence is a sensor wafer. Once all of the individual layers 206, 208, and 210 have been properly constructed as to architecture and sensor formation, they are aligned and bonded together to form substrate portion 102. Alignment is necessary as to achieve proper registration between sensing regions and channel regions in the microfluidic chip. Alignment is preferably achieved via an alignment jig or an alignment stage of a conventional bonding machine.

In an alternate embodiment, substrate portion 102 can be of a two layer construction having a cap layer 206 and a single silicon layer combining the features of individual silicon layers 208 and 210. In this embodiment, silicon layers 208 and 210 are formed in a single silicon wafer using DRIE to etch the flow channel 106 architecture in the wafer to a fixed depth. Typical channel 106 dimensions include a length of 1 cm, a width of up to 5 mm and depth of up to 500 $\mu$m. The carrier inlet 110 and outlet 122 are formed in the silicon wafer by etching through-holes using DRIE or conventional anisotropic etchants such as, for example, KOH. Alignment, of the wafer's features in this embodiment such as, for example, the flow channel, inlet and outlet dividers, inlet and outlet structures is advantageously achieved using conventional lithography.

Lithography is a technique by which a pattern on a mask is transferred to a film or substrate surface via a radiation sensitive material. The radiation may be optical, X-ray, electron beam or ion beam. For optical exposure, the radiation sensitive material is more commonly called a photoresist and the process is called photolithography. Photolithography includes two key steps: (1) pattern generation, and (2) pattern transfer. Pattern generation begins with mask design and layout using CAD software, from which a mask set is manufactured. A typical mask consists of a glass plate coated with a patterned chromium film. Pattern transfer typically includes: (i) dehydration and priming of the substrate surface, (ii) photoresist coating of the wafer, (iii) "soft bake" of the photoresist, (iv) exposure of the photoresist through the mask, (v) chemical development of the photoresist, (vi) wafer inspection, and (vii) post development bake or "hard bake". After hard bake, the mask pattern has been completely transferred to the photoresist.

Following hard bake, the desired pattern is transferred from the photoresist to the underlying film or wafer by a process known as etching. Etching is defined as the selective removal of unwanted regions of a film or substrate and is used to delineate patterns, remove surface damage, clean the surface, and fabricate three-dimensional structures. Semiconductors, metals, and insulators can all be etched with the, appropriate etchant. The two main categories are wet chemical and dry etching. As the name implies, wet chemical etching involves the use of liquid reactants to etch the desired material. Dry etch processes range from physical sputtering and ion beam milling to chemical plasma etching. Deep Reactive ion etching, the most common dry etch technique, uses a plasma of reactant gases to etch the wafer and, thus, is performed at low pressure in a vacuum chamber.

Hence, the two wafer embodiment provides simplicity in that there is only one wafer within which the flow channel, divider, and inlet and outlet architectures are formed thereby eliminating alignment during bonding of the three wafer embodiment. However, the three wafer embodiment provides for easier sensor fabrication since the sensor wafer is not etched with the flow architecture including the flow channel, inlet and outlet flow dividers, and inlets and outlets.

Still referring to FIGS. 2, 3, and 4, the cap layer 206 is bonded onto the silicon channel layer 208 to form the closed micro flow channel architecture. The cap layer 206 is preferably made of glass for providing optical inspection of the chip 100 during operation. In an alternative embodiment, cap layer 206 can be a silicon layer bonded onto layer 208.

So formed, substrate portion 102 is patterned with magnetic material to form magnetic structure 104 on the front and back of the flow channel 106. FIGS. 2, 3, and 4 illustrate different embodiments of magnetic structure 104. In all of the embodiments, the integrated magnetic structure 104 is formed by pattern plating molds and plating magnetically permeable materials such as, for example, nickel or iron. The molds are preferably formed from thick photoresist or polymide. The plating materials are preferably permalloy and nickel. The plating materials are preferably deposited via electroplating and electroless plating, where applicable, for the appropriate material.

FIG. 2 shows magnetic structure 104 in the form of two rectangular pole plates 202 and 204. FIG. 3 shows magnetic structure 104 in the form of two pole plates 302 and 304. Pole plates 302 and 304 have ends 306 and 308 that are machined into the shape of a hyperbola for optimizing the field generated by the magnetic structure 104. For a discussion of the hyperbolic structure for magnetic pole pieces, see U.S. Pat. No. 5,968,820 to Zborowski et al., which is hereby fully incorporated by reference. FIG. 4 shows magnetic structure 104 in the form of two pole plates 402 and 404. Pole plates 402 and 404 have ends 406 and 408 that approximate a hyperbola in a discrete step-wise fashion. More specifically, photoresist plating molds 410 and 412 have been patterned via laser micro-machining in a step-wise fashion (shown exaggerated in FIG. 4 for detail) to approximate a hyperbola. Once patterned, the photoresist plating molds 410 and 412 function as molds during the plating of magnetic material forming pole plates 402 and 404.

Figure 5:
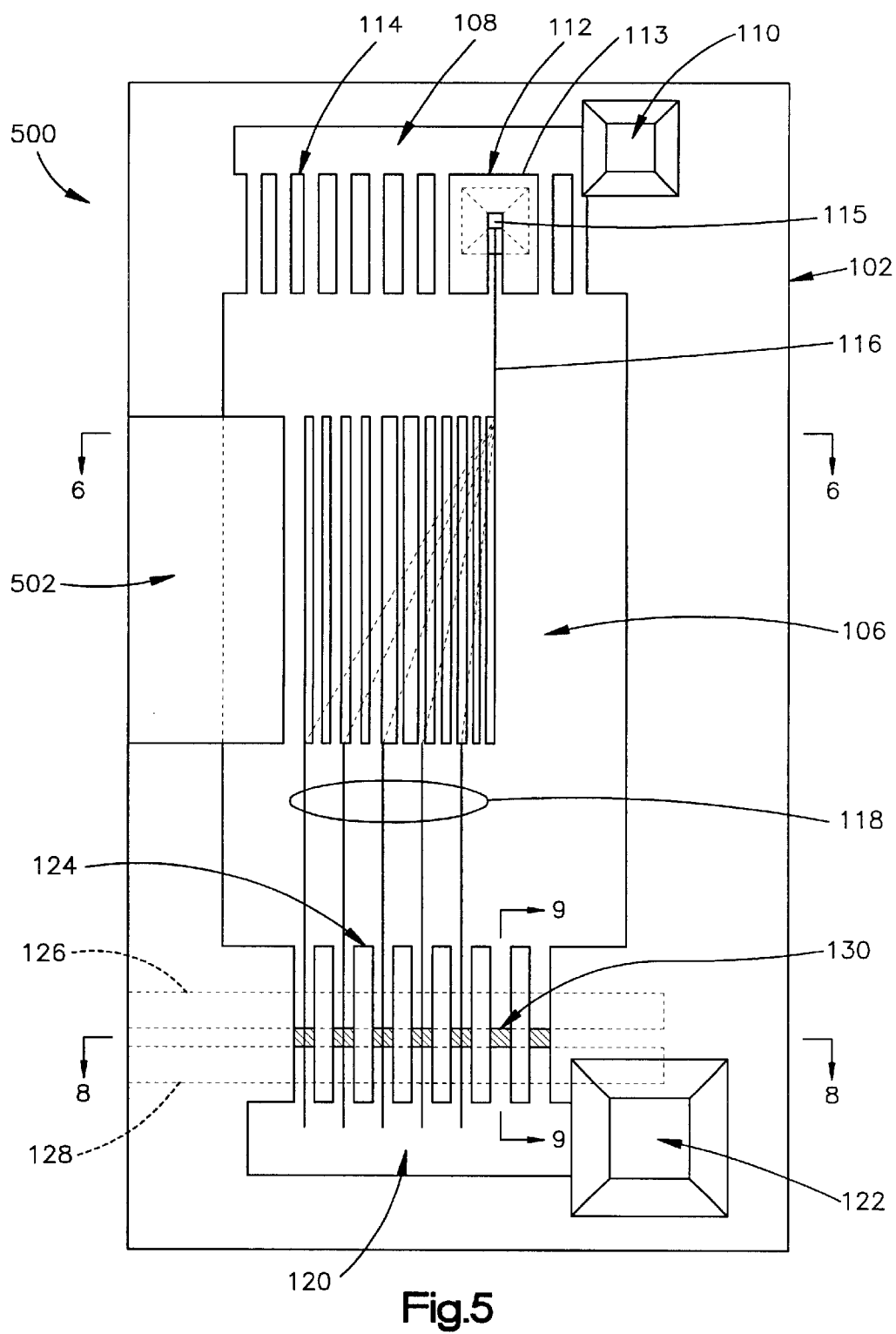
FIG. 5 is a plan view of a second embodiment of a microfluidic chip of the present invention having a discrete component magnetic structure.
Figure 6:
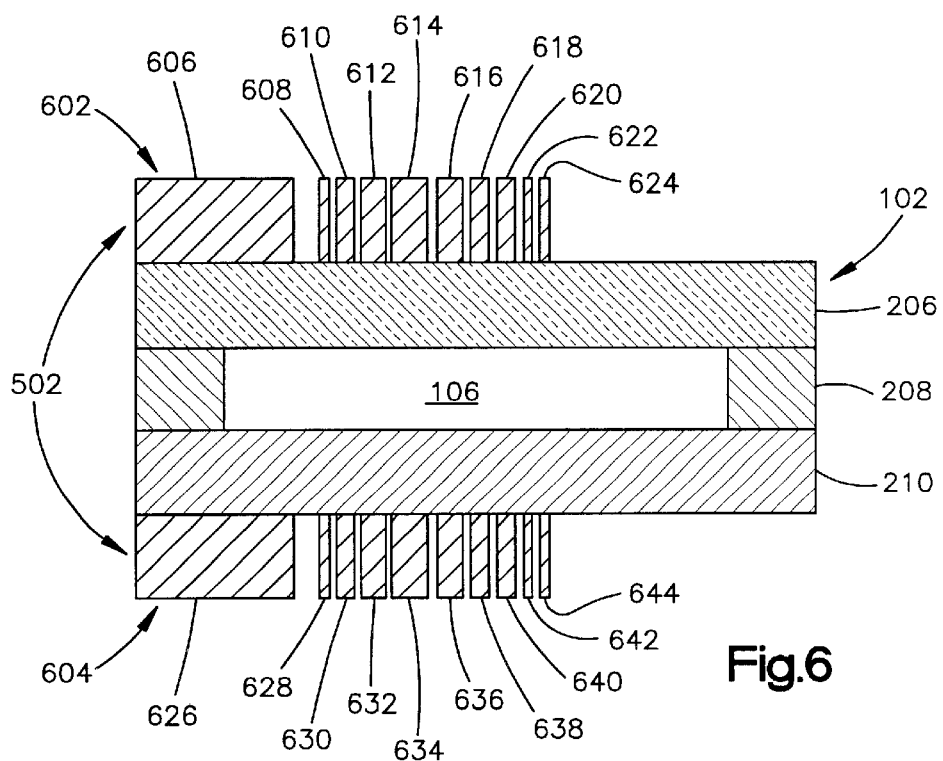
FIG. 6 is cross-sectional view taken along section line 6—6 of FIG. 5.

Referring now to FIGS. 5 and 6, a microfluidic chip 500 similar to chip 100 of FIG. 1 is shown. More specifically, chip 500 includes a magnetic structure 502 that includes pole pieces 602 and 604, each of which include a plurality of discrete pole pieces 606 through 644 separated by a plurality of gaps. Through such a configuration, pole pieces 606 through 644 approximate the magnetic field generated by the hyperbolically shaped poled pieces 302 and 304 of FIG. 3. In particular, the superposition of the field pattern from the discrete pole pieces 606 through 644 reasonably approximate the effect of hyperbolically shaped pole pieces 302 and 304. Each discrete pole piece maintains an orthogonal or "Manhattan" geometry, which simplifies fabrication. In the embodiment shown, pole pieces 606 through 644 have a common length and height, but varying widths as shown in FIG. 6. Hence, by having one or more orthogonal geometries, the pole pieces 606 through 644 and the gaps therebetween can approximate hyperbolically shaped pole pieces and produce a substantially uniform magnetic field in flow channel 106. However, it should also be noted that slight deviations from such "Manhattan" geometry are contemplated to improve the uniform force field distribution across flow channel 106. While twenty (20) discrete pole pieces are shown in FIG. 6, it should be understood that more or less pole pieces can be used—the main objective being to provide a uniform force distribution across flow channel 106. Once the pole pieces are constructed, a magnetomotive force is provided through a permanent external magnet connected to the pole plates or pieces by either placing the microfluidic chip inside a uniform magnetic field to induce magnetization, or by plating permanent magnets in place of the pole pieces.

Figure 7:
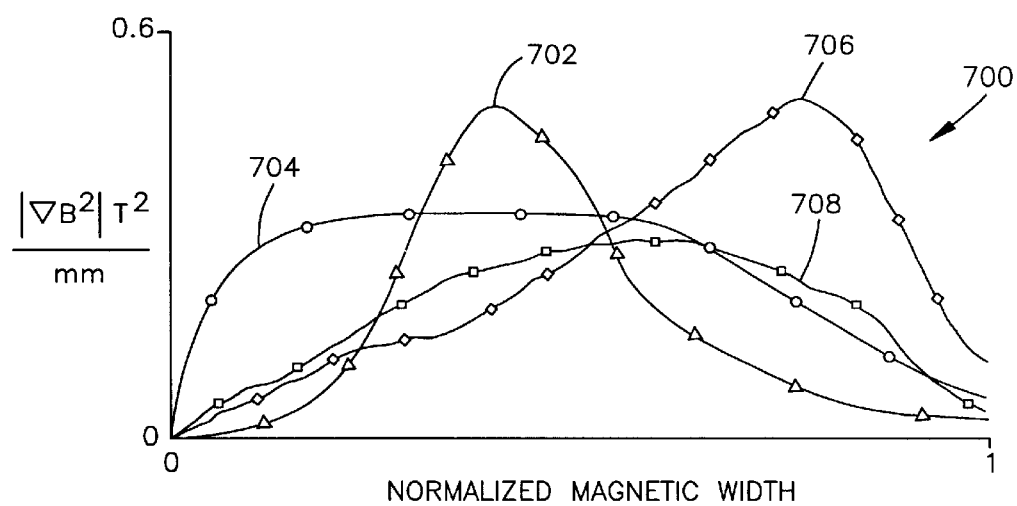
FIG. 7 is graph illustrated the magnetic field characteristic of the magnetic structures of FIGS. 2, 3, 4, and 6.

Referring now to FIG. 7, a graph 700 showing the proportional force $|\nabla B^2|$ as a function of normalized magnetic width for the magnetic structure embodiments of FIGS. 2, 3, 4, and 6 is illustrated. In particular, graph 702 represents the field generated by the magnetic structure 104 of FIG. 2. Graph 704 represents the field generated by the magnetic structure 104 of FIG. 3. Graphs 706 and 708 represent the field generated by two different discrete pole plate designs constructed according to magnetic structure 502 of FIGS. 5 and 6. Graph 706 and 708 illustrate that the superposition of the field pattern generated by the discrete pole piece embodiment of magnetic structure 502 can be used to generate a plurality of different field characteristics. More particularly, graph 708 illustrates that the discrete pole piece embodiment of magnetic structure 502 can be used to approximate the uniform force distribution generated by the hyperbolically shaped pole pieces 302 and 304 of FIG. 3.

Figure 8:
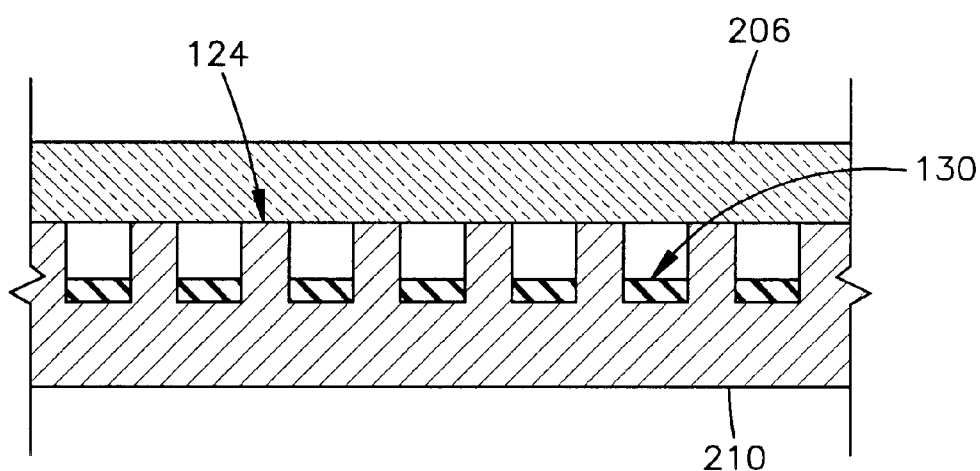
FIG. 8 is a partial cross-sectional view of a bioferrograph portion of microfluidic chip 100 and 500 taken along section line 8—8 of FIGS. 1 and 5.

Illustrated in FIG. 8 is a partial cross-sectional view taken along section lines 8—8 of FIGS. 1 and 5. More specifically FIG. 8 shows a cross-section of the bioferrograph cell collector region implemented with the two layer approach earlier discussed (i.e., cap layer 206 and a single silicon layer combining layers 208 and 210 into a single layer 210). As shown and described earlier, silicon layer 210 is preferably DRIE etched to form the divider architecture such as, for example, outlet manifold divider 124. Cap layer 206 is then bonded to silicon layer 210, as earlier discussed.

Alternately, the three wafer implementation may be employed wherein the divider architecture such as, outlet manifold divider 124, is implemented on a separate silicon wafer (e.g., layer 208) and the three wafers are bonded together, as earlier discussed.

Figure 9:
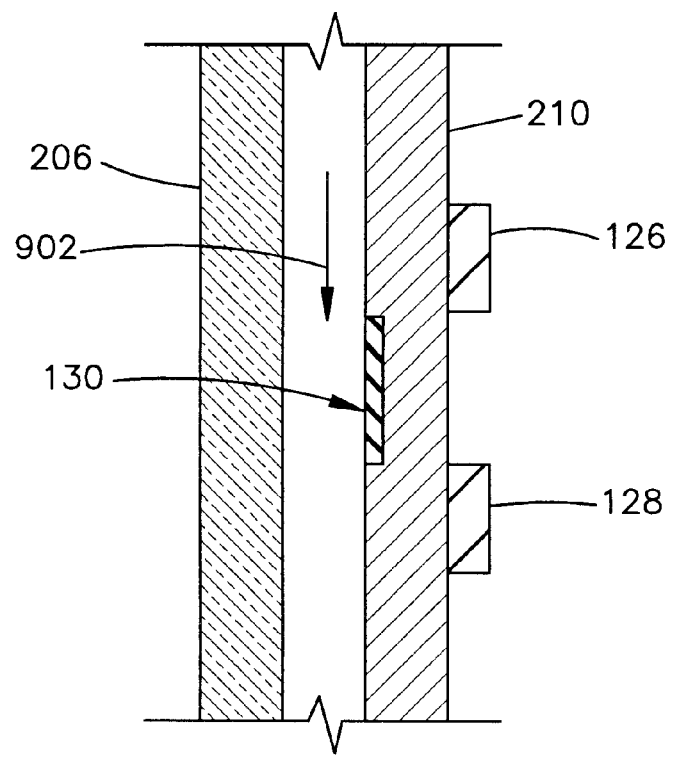
FIG. 9 is a partial cross-sectional view of the bioferrograph portion of microfluidic chip 100 and 500 taken along section line 9—9 of FIGS. 1 and 5.

FIG. 9 illustrates a partial cross-section taken through section lines 9—9 of FIGS. 1 and 5. More specifically, FIG. 9 illustrates the particle or fluid flow 902 across sensor 130, which resides between the outlet flow dividers. Magnets or pole pieces 126 and 128 are formed on the backside of silicon layer 210 and are of the same or similar materials and construction as magnetic structure 104.

Figure 10:
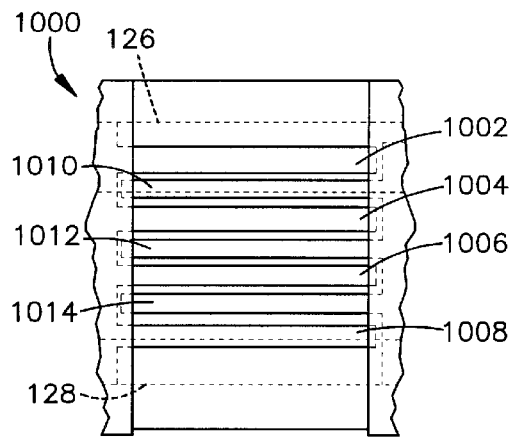
FIGS. 10–15 illustrate plan and partial cross-sectional views of three embodiments of cell sensors of the present invention.
Figure 11:
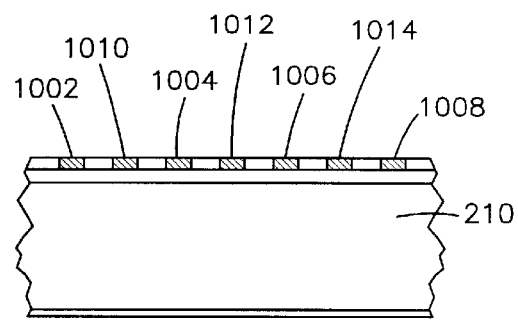

Referring now to FIGS. 10–15, three embodiments of a sensor of the present invention are shown in plan and partial cross-section. Referring now more particularly to FIGS. 10 and 11, an impedance-type cell sensor 1000 is illustrated. Impedance-type cell sensor 1000 has a plurality of polysilicon electrodes such as, for example, electrodes 1002 through 1014, overlapping the inter-polar gap between magnets or pole pieces 126 and 128. The electrodes 1002–1014 are buried within the flow channel floor thereby eliminating any flow disturbances that might arise due to differences in planar geometry between the flow channel and the sensor. As magnetically susceptible cells are deposited on the floor of the channel and on the sensor, the impedance between the plurality of electrodes 1002–1014 changes thereby providing an indication of the quantity of cells deposited. External circuitry (not shown), which can be of conventional design, is used to measure the change in impedance.

Figure 12:
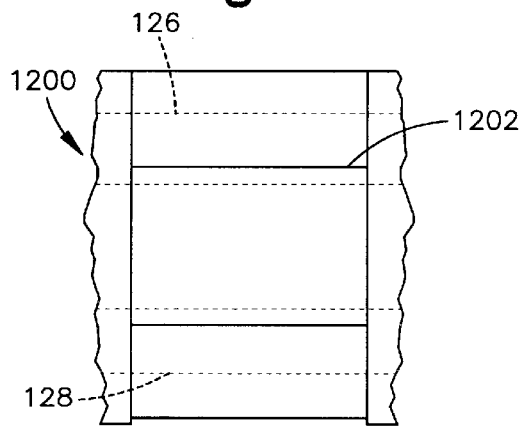
Figure 13:
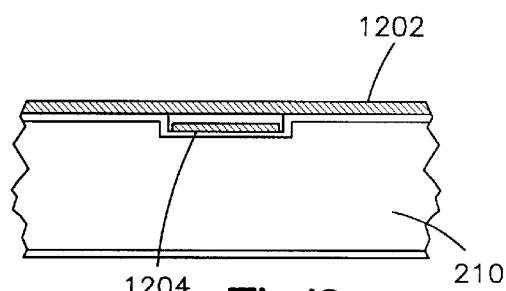

FIGS. 12 and 13 illustrate a second embodiment of a cell sensor of the present invention. More specifically, FIGS. 12 and 13 illustrate a resonant-type cell sensor 1200. Resonant-type cell sensor 1200 includes a first polysilicon layer 1202 and a second polysilicon layer 1204 spaced apart therefrom. Polysilicon layers 1202 is capacitively driven at its resonant frequency by external circuitry (not shown), which can be of convention design. Polysilicon layer 1204 senses the vibration frequency of polysilicon layer 1202. As cells deposit on polysilicon layer 1202, its resonant vibration frequency changes, which is detected by polysilicon layer 1204 and monitored by the external circuitry.

Figure 14:
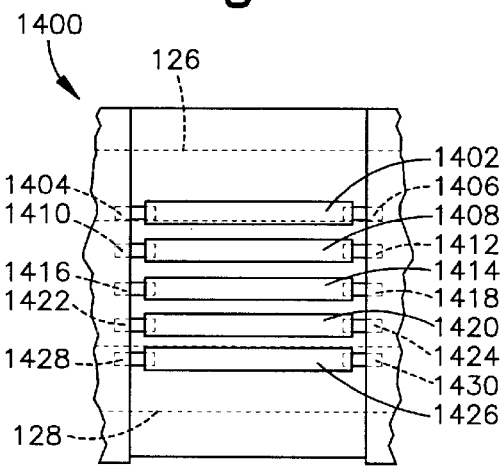
Figure 15:
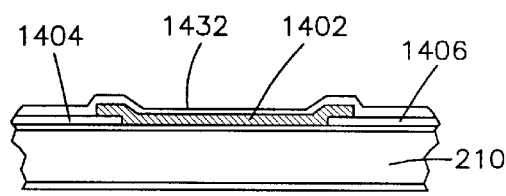

FIGS. 14 and 15 illustrate a third embodiment of a cell sensor in the form of a giant magnetoresistive (GMR) sensor 1400. In this regard, many metals exhibit a phenomenon called magnetoresistance (MR), which means that they show slight changes in electrical resistance when placed in a magnetic field. By designing materials made up of very thin layers of such metals, this effect can be amplified. In this regard, GMR sensor 1400 has a plurality of sensing portions such as, for example, portions 1402, 1408, 1414, 1420, and 1426. GMR materials generally include multi-layered substrates having magnetic material layers separated by non-magnetic material layers such as, for example, cobalt and copper. Advanced GMR materials include multi-layered substrates having pinned and unpinned magnetic orientations. Pinned magnetic orientations have electron spins that are fixed into given directions. Unpinned magnetic orientations have electron spins that are free to rotate directions.

GMR sensor 1400 also includes a plurality of polysilicon contacts such as, for example, contacts 1404, 1406, 1410, 1412, 1416, 1418, 1422, 1424, 1428, and 1430, for making electrical contact with the sensor portions so that external circuitry can monitor changes in the resistance of the sensor portions. The GMR sensor portions are preferably deposited by sputtering and are subsequently encased in a sputtered Nitride ($Si_3N_4$) layer 1432. As magnetically susceptible particles such as, for example, magnetically tagged cells, are deposited across the sensor portions, the resistance of the sensing portions changes in proportion thereto.

Figure 16:
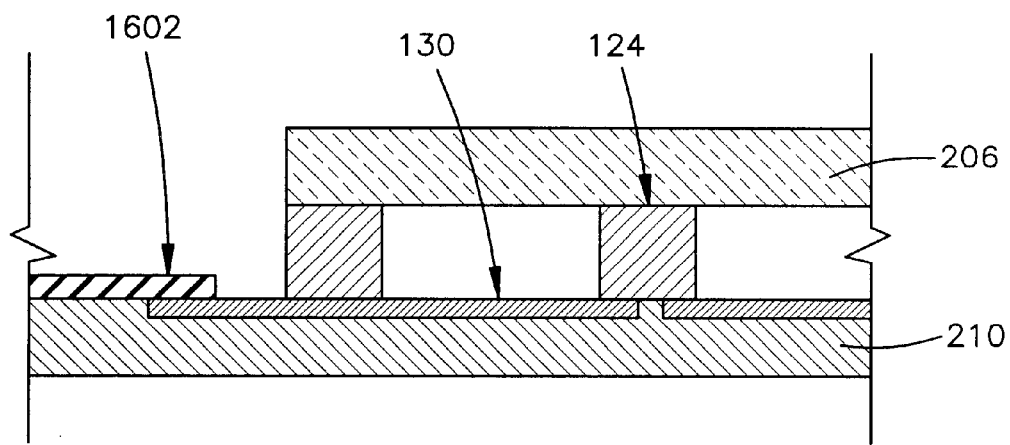
FIGS. 16 and 17 illustrate two embodiments of an electrical contact scheme of the present invention for providing external electrical connectivity to the cell sensors of FIGS. 10–15.
Figure 17:
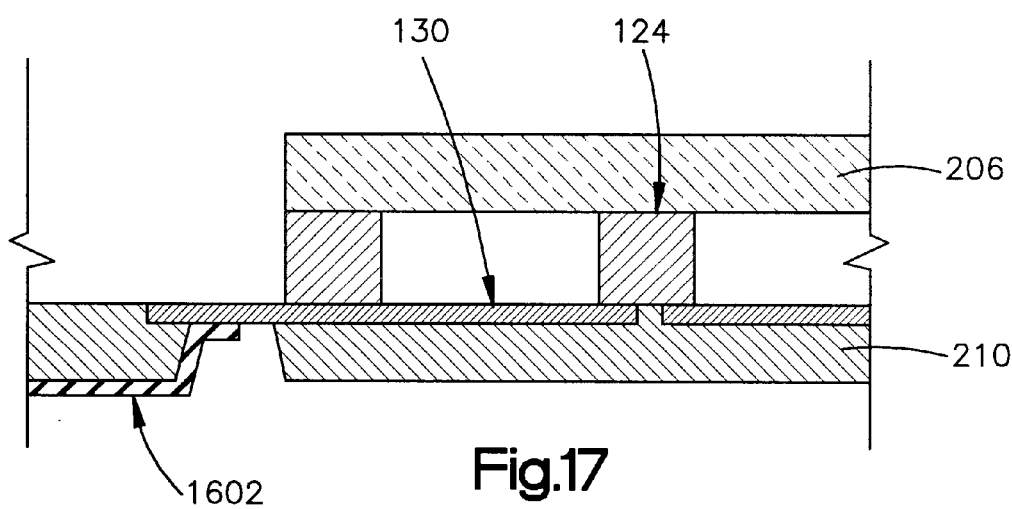

Referring now to FIGS. 16 and 17, two electrical contact schemes for the present invention are shown in cross-section. FIG. 16 illustrates a topside contact scheme with electrical contact 1602 contacting sensor 130. FIG. 17 illustrates a backside contact scheme with electrical contact 1602 contacting sensor 130 through a well formed in silicon layer 210. A third contact scheme (not shown) is to provide vias or through holes in silicon layer 210 for backside electrical connection to sensor 130. Contact 1602 is preferably made from doped polysilicon lines encapsulated in oxide or nitride and planarized.

Figure 18:
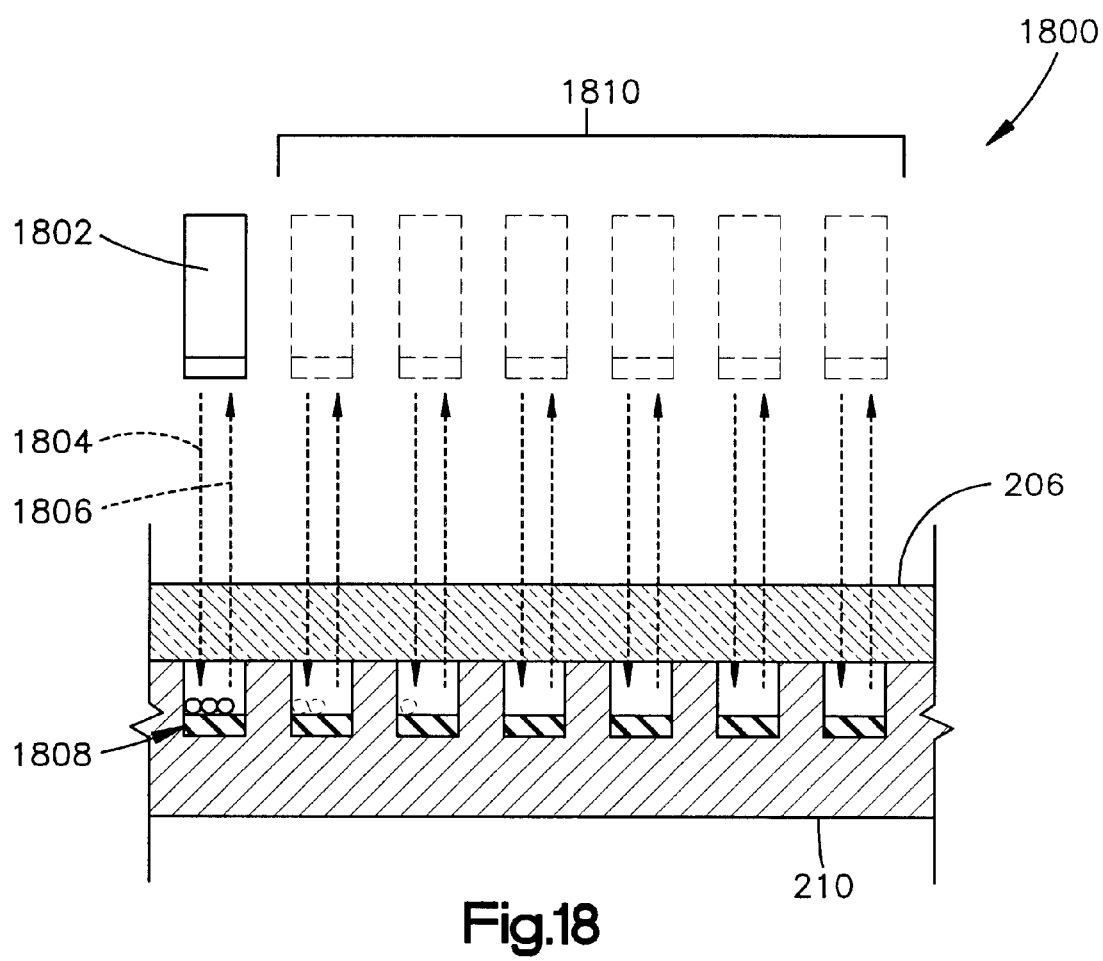
FIG. 18 illustrates a optical detection implementation of the present invention.

FIG. 18 illustrates an optical cell detection implementation 1800 of the present invention. The optical cell detection implementation 1800 takes advantage of cell markers that are both fluorescent and magnetic. More specifically, optical cell detection implementation 1800 is similar to the embodiment shown in FIG. 8, except that the cell sensors 130 of FIG. 8 have been replaced with photodiodes 1808 and a fluorescent light source 1802 is employed. In this regard, appropriately tagged cells are separated in the flow channel 106 and collected in bioferrograph portion of chip 100. The number of cells can be quantified by measuring the intensity of their fluorescent signal in response to optical excitation. The higher the intensity, the greater the number of cells collected. So configured, directs fluorescent light through glass layer 206 and into the bioferrograph toward photodiode 1808. Photodiode 1808 then senses the intensity of the cells' fluorescence. In this regard, an individual fluorescent light sources can be used for each bioferrograph collector region or single fluorescent light source 1802 can be scanned across the collector regions, as generally shown at 1810.

In an alternative embodiment, photodiode 1808 can be integrated with fluorescent light source 1802 so that the excitation source and detection source are collocated. In this embodiment, optical fibers can be used to separately direct fluorescent light to the bioferrograph and return any excited luminosity from the cells. This configuration of optical fibers can be scanned over the entire bioferrograph region interrogating for cell luminosity.

So configured, the bioferrograph portion employs fluorescence detection through the combination of combining fluorescent and magnetic tags on a cell labeling antibody. The fluorescence is quantitatively detected by directing fluorescent light onto the cells and measuring the intensity of the light reflected from the labeled cells. The light intensity is then correlated with a quantity of detected cells or, pathogens through a computerized database.

Figure 19:
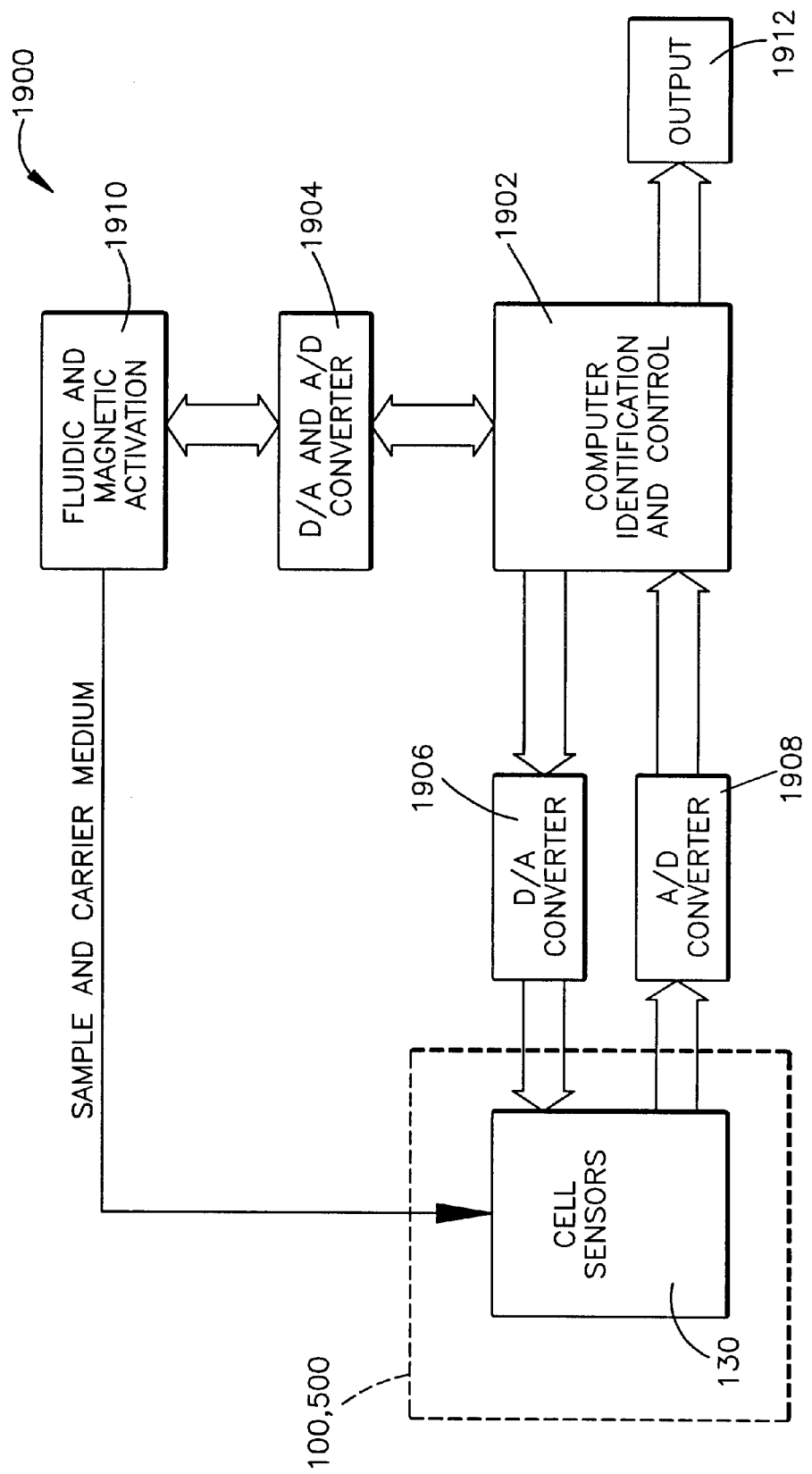
FIG. 19 illustrates a computerized system of the present invention.

Illustrated in FIG. 19 is a computerized cell identification and sorting system 1900 of the present invention. The system 1900 has a computer identification and control unit 1902, a plurality of Analog-to-Digital (A/D) and Digital-to-Analog (D/A) converters 1904, 1906, and 1908. The system 1900 and, more particularly, fluidic and magnetic activation unit 1810 further include a plurality of micro-fluidic components such as, for example, electrically controllable pumps and switching circuits for making and breaking electrical connections (not shown). Once activated, the pumps introduce the carrier and sample fluids into the flow channel from one or more reservoirs (not shown).

The identification and control unit 1902 is preferably a microprocessor-based system such as, for example, a personal or notebook computer. The computer preferably includes conventional components such as, for example, a micro-processor, memory, input/output data buses, a display, one or more computer readable medium devices such as hard and floppy disk and CD-ROM drives, and user input devices such as a keyboard and mouse device. The identification and control unit 1902 is in circuit communication with A/D and D/A converters 1904, 1906, and 1908 via the one or more input/output data buses.

In operation, the identification and control unit 1902 sends a start command to fluidic and magnetic activation component 1910. This commands activates or turns on the magnetic field and causes the sample and carrier fluids to be introduced in to, the flow channel 106 (see FIG. 1). D/A and A/D converter 1904 also sends and receives information from the fluidic and magnetic activation component 1910 regarding sample and carrier medium flow rates. The identification and control unit 1902 also sends a start command or signal to D/A converter 1906 to activate or turn on sensors 130 and any associated magnetic components (e.g., magnetic pole pieces 126 and 128). As cells flow through flow channel 106 and deposit on sensors 130, sensors 130 produce a spectrum signal unique to the identity and quantity of magnetically-labeled cells. Since the spectrum signal is in analog format, A/D converter 1908 converts it to a digital format and transfers it to identification and control unit 1902. In the identification and control unit 1902, the spectrum data is analyzed by software routines to identify and quantify the cells by matching the spectrum to a preprogrammed library. The results may be displayed on an appropriate output 1912 such as, for example, a display monitor or printer. Upon completion, the identification and control unit 1902 sends stop signals to the fluidic and magnetic activation unit 1910 and sensors 130.

The components of system 1900 can take the form of any number of physical configurations. For example, microfluidic chip 100 (FIG. 1) or 500 (FIG. 5) can be implemented on a computer card having A/D and D/A converters 1904, 1906, and 1908, and fluidic and magnetic activation unit 1910 integral therewith. In such an embodiment, the computer card can simply be plugged into a personal or notebook computer for analysis.

In another embodiment, micro-fluidic chip 100 (FIG. 1) or 500 (FIG. 5) can be removable components of a permanent computer accessory device having A/D and D/A converters 1904, 1906, and 1908, and fluidic and magnetic activation unit 1910 thereon. In this embodiment, a new micro-fluidic chip 100 (FIG. 1) or 500 (FIG. 5) is inserted for each new analysis. In either embodiment, computer can be via either parallel or serial communication protocols including, for example, RS-232, Universal Serial Bus (USB) and/or Firewire (IEEE 1394 High Performance Serial Bus) communications.

While the present invention has been illustrated by the description of embodiments thereof, and while the embodiments have been described in considerable detail, it is not the intention of application to restrict or in any way limit the scope of the appended claims to such detail. Additional advantages and modifications will readily appear to those skilled in the art. For example, the system can be made from glass, ceramic, plastic, stainless steel and aluminum substrates in addition to silicon. Furthermore, the channel and wafer architecture can be formed by fabrication techniques other than DRIE including molding, wire-EDM, laser cutting, and conventional machining. Therefore, the invention, in its broader aspects, is not limited to the specific details, the representative apparatus, and illustrative examples shown and described. Accordingly, departures may be made from such details without departing from the spirit or scope of the applicant's general inventive concept.

We claim:

1. A particle identification system comprising:
   (a) a substrate having a topside portion, backside portion and a flow system, the flow system comprising a flow channel for accepting the flow of a stream of particles to be identified;
   (b) a magnetic structure in physical communication with the topside and backside portions of the substrate, the magnetic structure comprising at least two pole pieces, each pole piece comprising a plurality of discrete pole pieces; the magnetic structure generating a magnetic field for acting on magnetically susceptible particles in the stream; and
   (c) a bioferrograph for identifying the presence of magnetically susceptible particles.

2. The system of claim 1 wherein the substrate comprises a material selected from the group consisting of: silicon, glass, ceramics, and plastics.

3. The system of claim 1 wherein the flow system further comprises an inlet portion and an outlet portion, and the inlet portion and the outlet portion each comprise a plurality of flow dividers.

4. The system of claim 3 wherein the inlet portion comprises a carrier fluid inlet and a particle feed.

5. The system of claim 4 wherein the particle feed is disposed between the plurality of inlet flow dividers.

6. The system of claim 1 wherein the topside comprises a transparent glass layer.

7. A particle identification system comprising:
   (a) a substrate having a topside portion, backside portion, and a flow system, the flow system comprising a flow channel for accepting the flow of a stream of particles to be identified;
   (b) a magnetic structure in physical communication with the topside and backside portions of the substrate, the magnetic structure comprising at least two pole pieces, each pole piece comprising a plurality of discrete pole pieces; the magnetic structure generating a magnetic field for acting on magnetically susceptible particles in the stream; and
   (c) a bioferrograph for identifying the presence of magnetically susceptible particles, comprising a sensor portion and a magnetic portion, the sensor portion being disposed between the outlet flow dividers.

8. The system of claim 7 wherein the sensor portion comprises at least one impedance-type sensor.

9. The system of claim 8 wherein the impedance-type sensor comprises at least two electrodes for sensing contact with a particle.

10. The system of claim 7 wherein the sensor portion comprises at least one resonant-type sensor.

11. The system of claim 10 wherein the resonant-sensor comprises at least one resonating material for sensing contact with a particle.

12. The system of claim 7 wherein the sensor portion comprises at least one magnetoresistive sensor.

13. The system of claim 12 wherein the magnetoresistive sensor comprises at least one sensing section having first and second electrodes and a magnetoresistive material therebetween.

14. A particle identification system comprising:
   (a) a substrate, comprising a plurality of discrete layers of material and having a topside portion, backside portion, and a flow system, the flow system comprising a flow channel for accepting the flow of a stream of particles to be identified;

(b) a magnetic structure in physical communication with the topside and backside portions of the substrate, the magnetic structure comprising at least two pole pieces, each pole piece comprising a plurality of discrete pole pieces; the magnetic structure generating a magnetic field for acting on magnetically susceptible particles in the stream; and (c) a bioferrograph for identifying the presence of magnetically susceptible particles.

15. The system of claim 14 wherein each of the plurality of discrete layers within the substrate comprises a material selected from the group consisting of: silicon, glass, ceramics, and plastics.

16. The system of claim 15 wherein a first layer of the plurality of discrete layers comprises a first material and a second layer of the plurality of discrete layers comprises a second material.

17. The system of claim 14 wherein the flow system further comprises an inlet portion and an outlet portion, and the inlet portion and the outlet portion each comprise a plurality of flow dividers.

18. The system of claim 17 wherein the inlet portion comprises a carrier fluid inlet and a particle feed.

19. The system of claim 18 wherein the particle feed is disposed between a plurality of inlet flow dividers.

20. The system of claim 14 wherein the topside comprises a transparent glass layer.

21. The system of claim 14 wherein the flow channel is located between the topside portion and the backside portion of the substrate.

* * * * *

UNITED STATES PATENT AND TRADEMARK OFFICE
CERTIFICATE OF CORRECTION

PATENT NO. : 6,623,984 B1
DATED : September 23, 2003
INVENTOR(S) : Aaron J. Fleischman et al.

It is certified that error appears in the above-identified patent and that said Letters Patent is hereby corrected as shown below:

Title page,
Item [73], Assignee, insert -- Ohio State University
Columbus, OH (US) --

Signed and Sealed this

Fourteenth Day of December, 2004

JON W. DUDAS
*Director of the United States Patent and Trademark Office*